(12) United States Patent
Green

(10) Patent No.: US 9,498,353 B2
(45) Date of Patent: Nov. 22, 2016

(54) GROUND CONTACT DEVICE

(71) Applicant: Travis Green, Canyon Lake, TX (US)

(72) Inventor: Travis Green, Canyon Lake, TX (US)

( * ) Notice: Subject to any disclaimer, the term of this patent is extended or adjusted under 35 U.S.C. 154(b) by 94 days.

(21) Appl. No.: 14/150,645

(22) Filed: Jan. 8, 2014

(65) Prior Publication Data

US 2014/0195009 A1    Jul. 10, 2014

Related U.S. Application Data

(60) Provisional application No. 61/750,494, filed on Jan. 9, 2013.

(51) Int. Cl.
*A61F 2/66* (2006.01)

(52) U.S. Cl.
CPC ............ *A61F 2/66* (2013.01); *Y10T 29/49204* (2015.01)

(58) Field of Classification Search
CPC ............. A61F 2/66; A61F 2002/6614; A61F 2002/665
USPC ................................................ 623/77, 82–86
See application file for complete search history.

(56) References Cited

U.S. PATENT DOCUMENTS

| | | | | | |
|---|---|---|---|---|---|
| 1,348,531 | A | * | 8/1920 | Amadio | A61H 3/0288 135/82 |
| 5,593,455 | A | * | 1/1997 | Phillips | A61F 2/66 623/47 |
| 5,653,767 | A | * | 8/1997 | Allen | A61F 2/66 623/52 |
| 5,713,382 | A | * | 2/1998 | Midcap | A45B 9/04 135/44 |
| 8,739,807 | B2 | * | 6/2014 | Taylor | A61H 3/0288 135/77 |

\* cited by examiner

*Primary Examiner* — Bruce E Snow
(74) *Attorney, Agent, or Firm* — DLA Piper LLP (US)

(57) ABSTRACT

A ground contact device having a module with at least a portion of the module's outer surface being curved. The ground contact device also having a planar surface, oriented in a plane parallel to a surface suitable for walking, on the module's inside surface. In addition, the planar surface contains a plurality of prosthetic mount holes.

12 Claims, 21 Drawing Sheets

GROUND CONTACT DEVICE

CROSS-REFERENCE TO RELATED APPLICATIONS

This application claims the benefit of U.S. Provisional Application No. 61/750,494, filed Jan. 9, 2013, entitled Stump Armour, which is hereby incorporated by reference in its entirety.

BRIEF DESCRIPTION OF THE SEVERAL VIEWS OF THE DRAWINGS

The accompanying drawings, incorporated herein as part of the specification, illustrate the presently disclosed subject matter, and with the description, serve to explain the principles of the disclosed subject matter and to enable a person skilled in the pertinent art to make and use the disclosed subject matter.

DETAILED DESCRIPTION OF EMBODIMENTS

Figure 1:
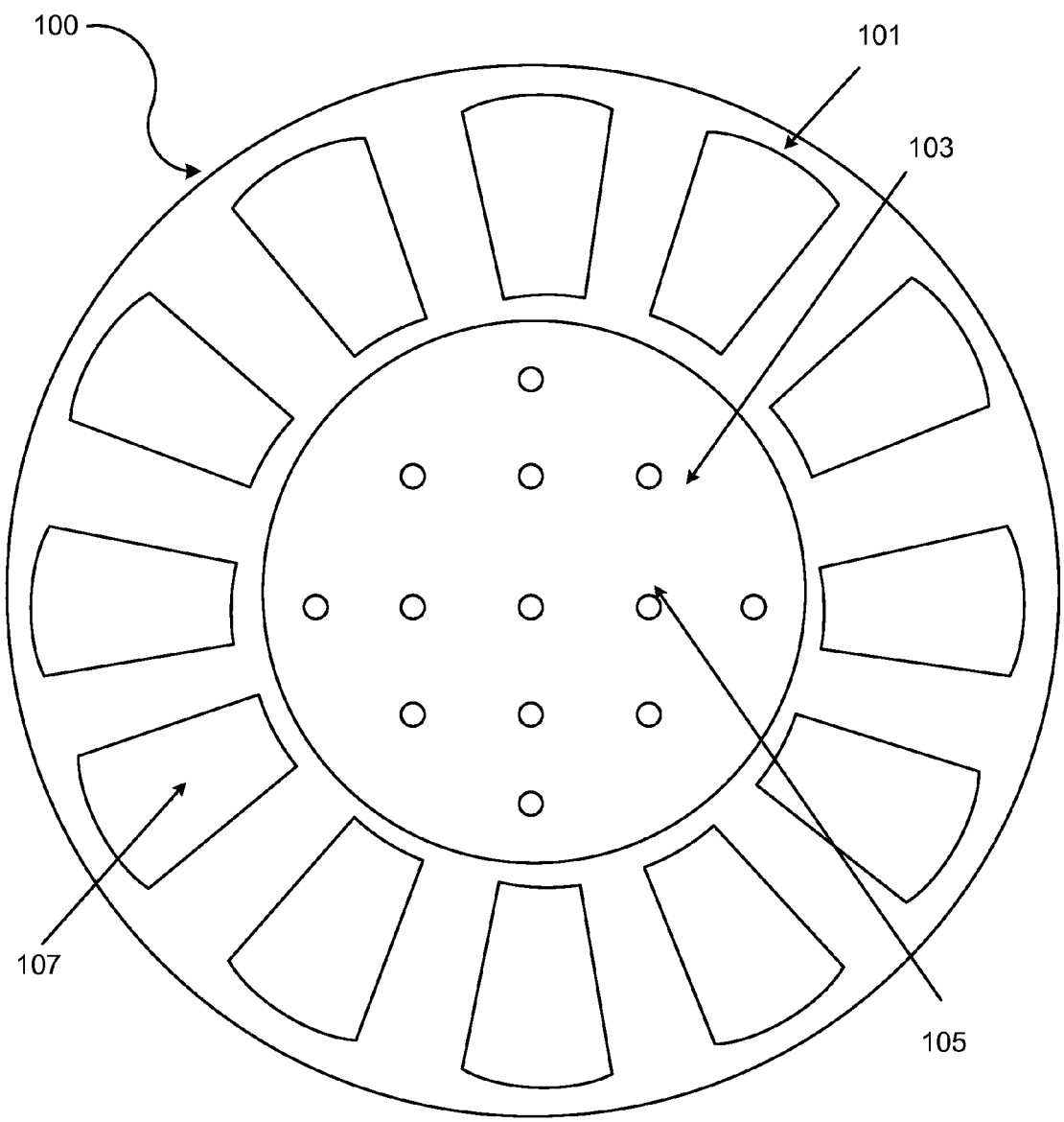
FIG. 1 is a top plan view of a ground contact device according to a first embodiment of the presently disclosed subject matter with twelve openings about its periphery.
Figure 2:
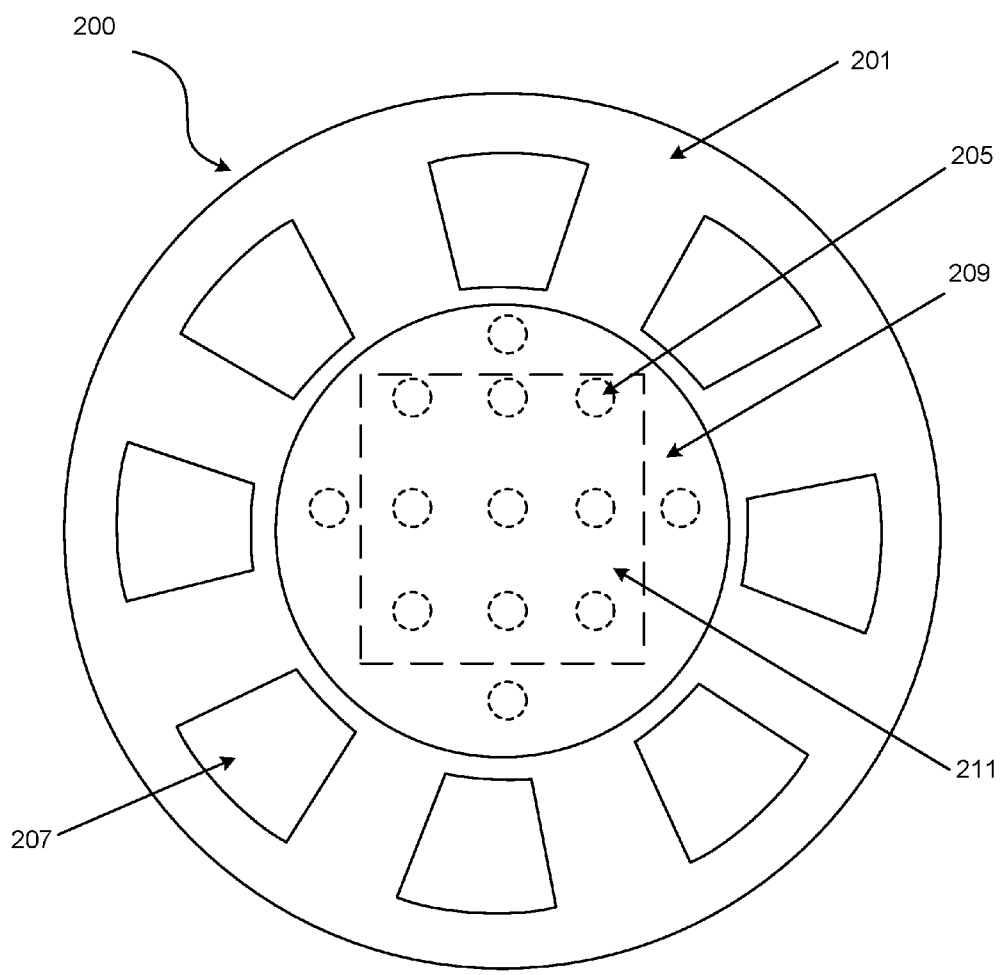
FIG. 2 is a bottom plan view of a ground contact device according to a second embodiment of the presently disclosed subject matter, similar to the first embodiment except with eight opening about its periphery.
Figure 3:
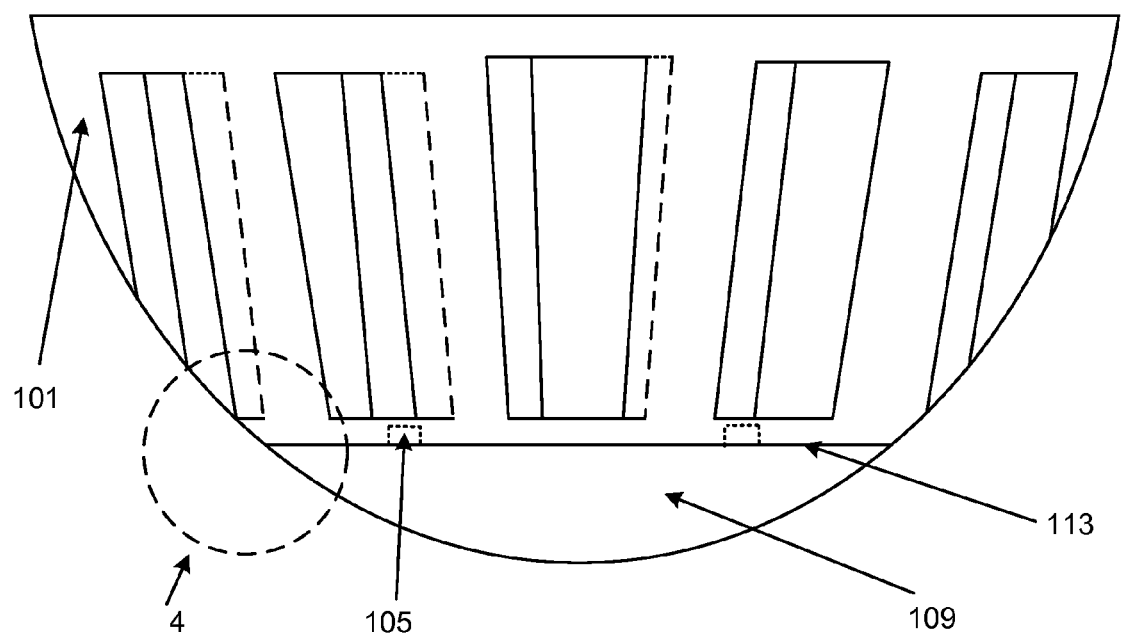
FIG. 3 is a side elevational view of a ground contact device according to the first embodiment of the presently disclosed subject matter.

As seen in FIGS. 1-3, ground contact device 100, 200 comprises wall module 101, 201 and base module 109, 209 attached to wall module 101, 201. Wall module 101, 201 defines openings 107, 207. There may be any number of openings 107, 207 and they may have any shape and arrangement. For example, the openings 107 may have any shape that provides access to the prosthetic mount for adjustments, including but not limited to, shapes that are rectangular, square, triangular, or circular. The embodiment of FIGS. 1 and 3 includes twelve openings 107, whereas FIG. 2 includes eight openings 207. As seen in FIGS. 1-3, wall module 101, 201 comprises planar member 103, 203, which contains mount holes 105, 205. As seen in FIGS. 1 and 2, the mount holes 105, 205 in ground contact device 100, 200 comprise a three by three square pattern with four additional mount holes located around the three by three square pattern, such that there is an additional mount hole centered on the outside of each side of the three by three pattern. Mount holes 105, 205 may comprise any other suitable arrangement. In addition, mount holes 105 may be threaded for use with fasteners such as, but not limited to, screws, or may be unthreaded for use with fasteners such as, but not limited to, bolts.

Figure 8:
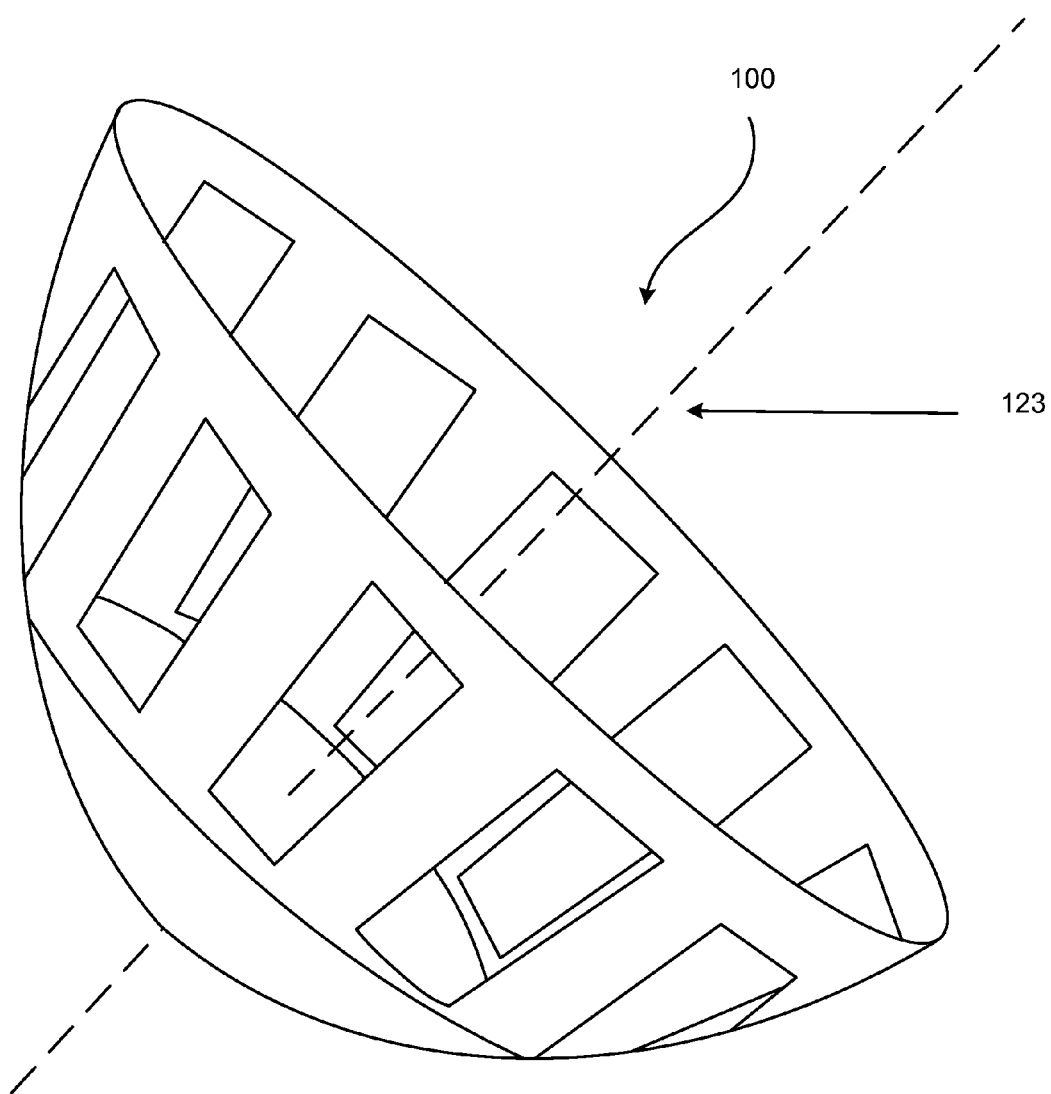
FIG. 8 is a perspective view of a ground contact device according to a fourth embodiment of the presently disclosed subject matter, similar to the first embodiment except with ten openings about its periphery.
Figure 9:
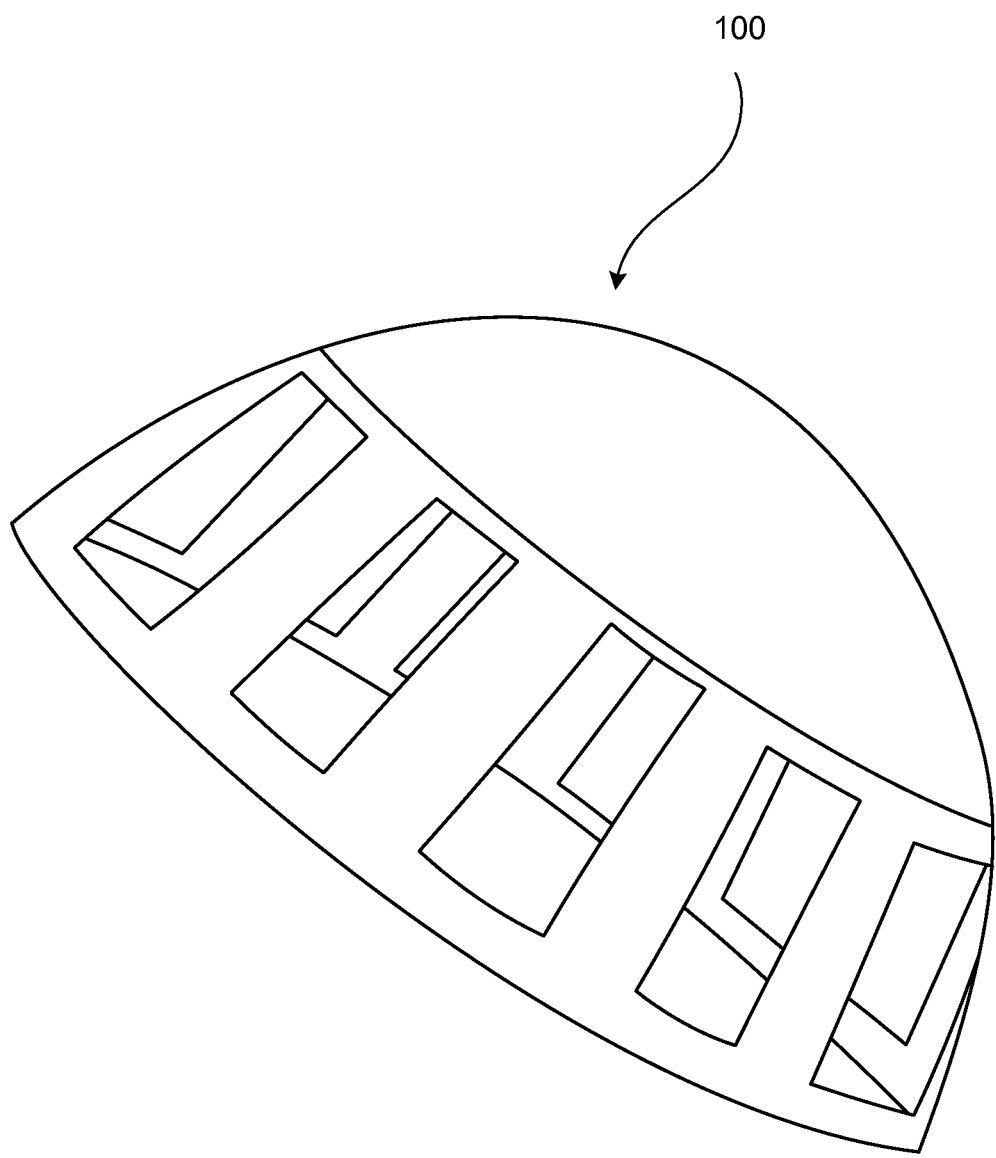
FIG. 9 is a perspective view of a ground contact device according to the first embodiment of the presently disclosed subject matter.
Figure 10:
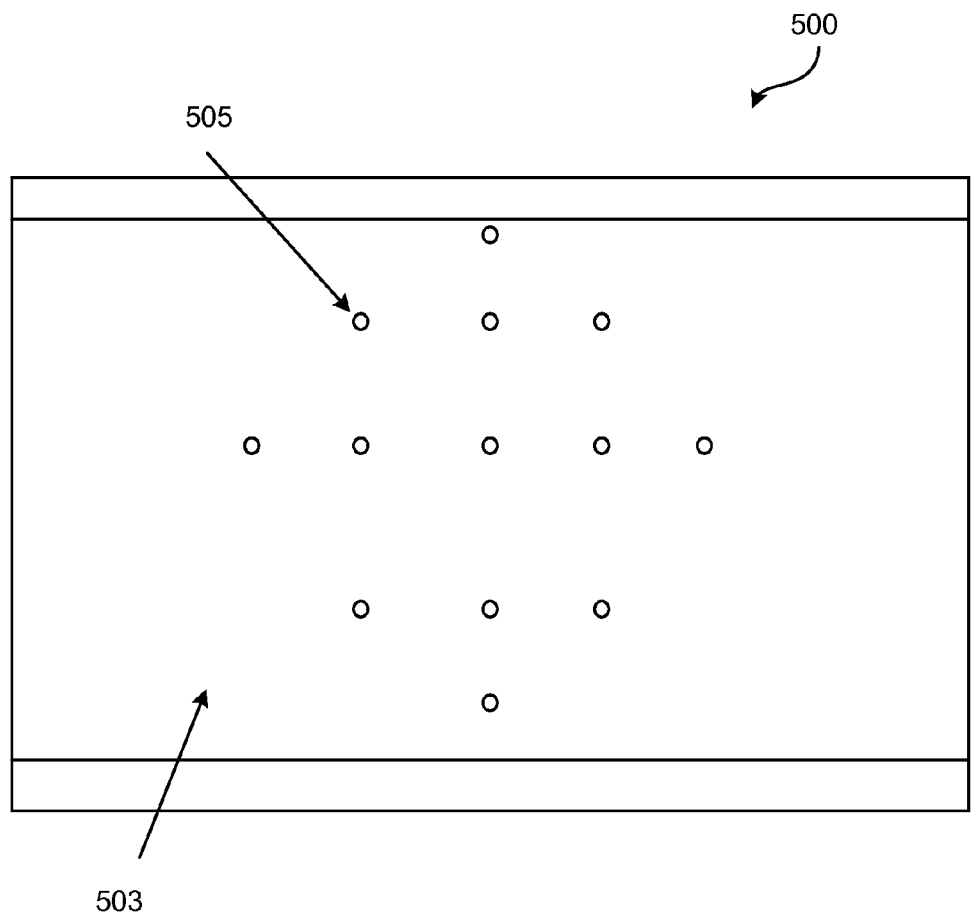
FIG. 10 is a top plan view of a ground contact device according to a fifth embodiment of the presently disclosed subject matter.
Figure 11:
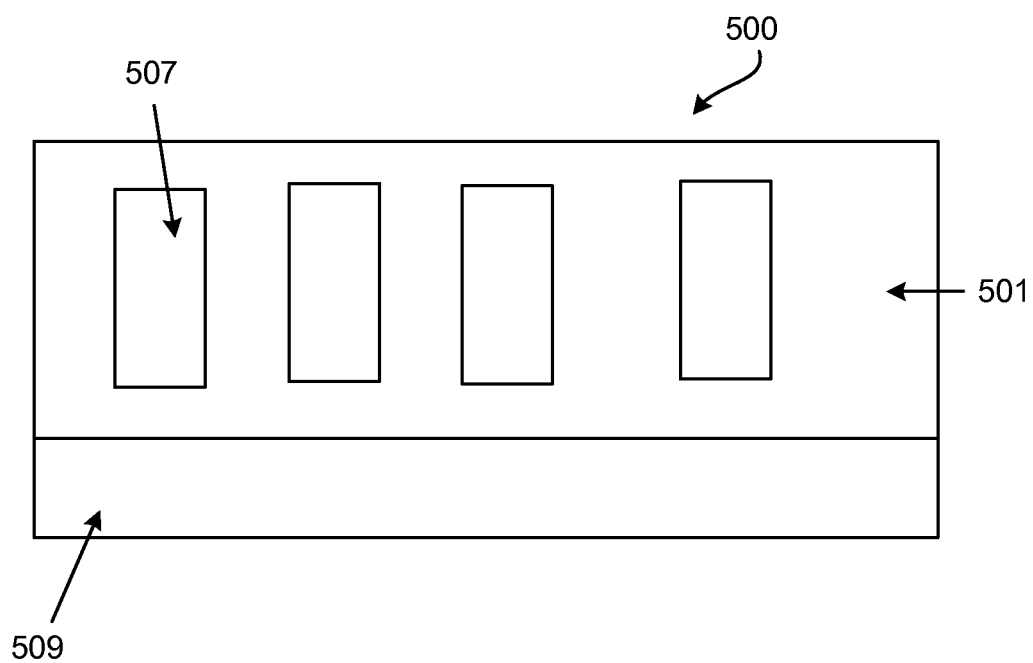
FIG. 11 is a side elevational view of a ground contact device according to the fifth embodiment of the presently disclosed subject matter.
Figure 12:
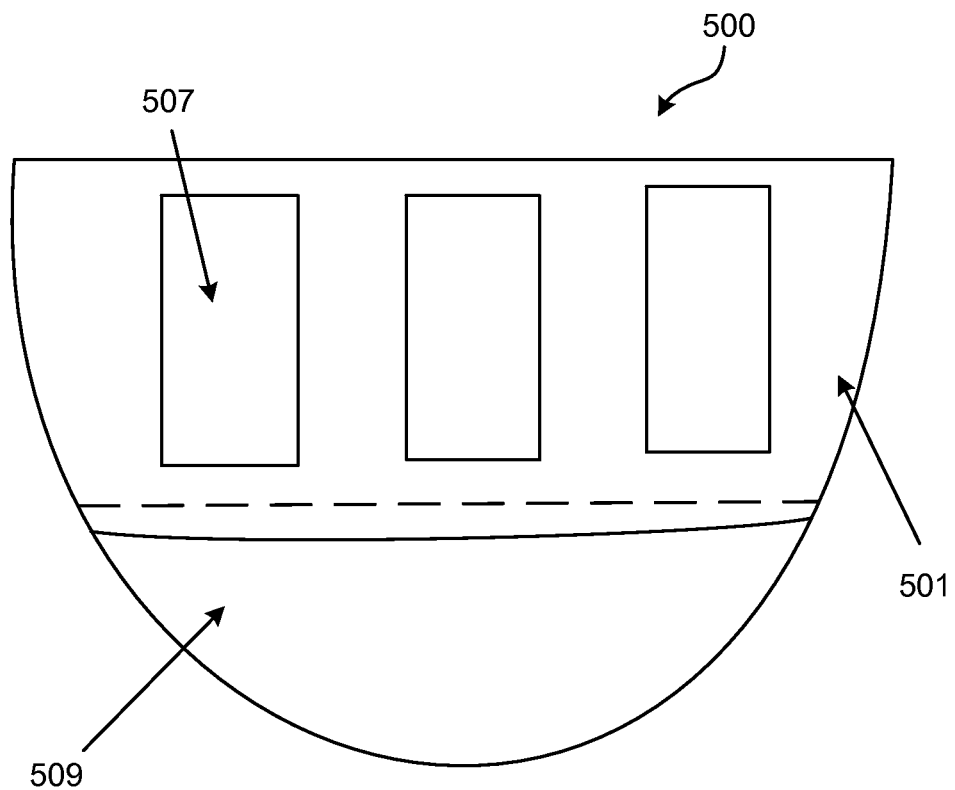
FIG. 12 is an end/side elevational view of a ground contact device according to the fifth embodiment of the presently disclosed subject matter.
Figure 13:
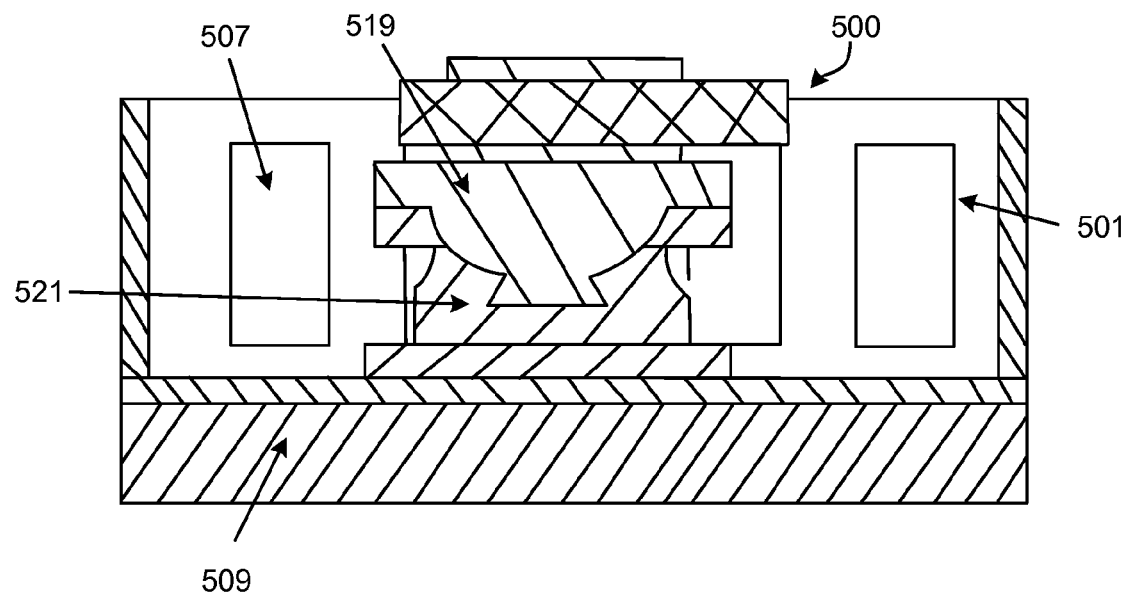
FIG. 13 is a cross sectional view of the ground contact device according to the fifth embodiment coupled to a relatively short prosthetic mount.
Figure 14:
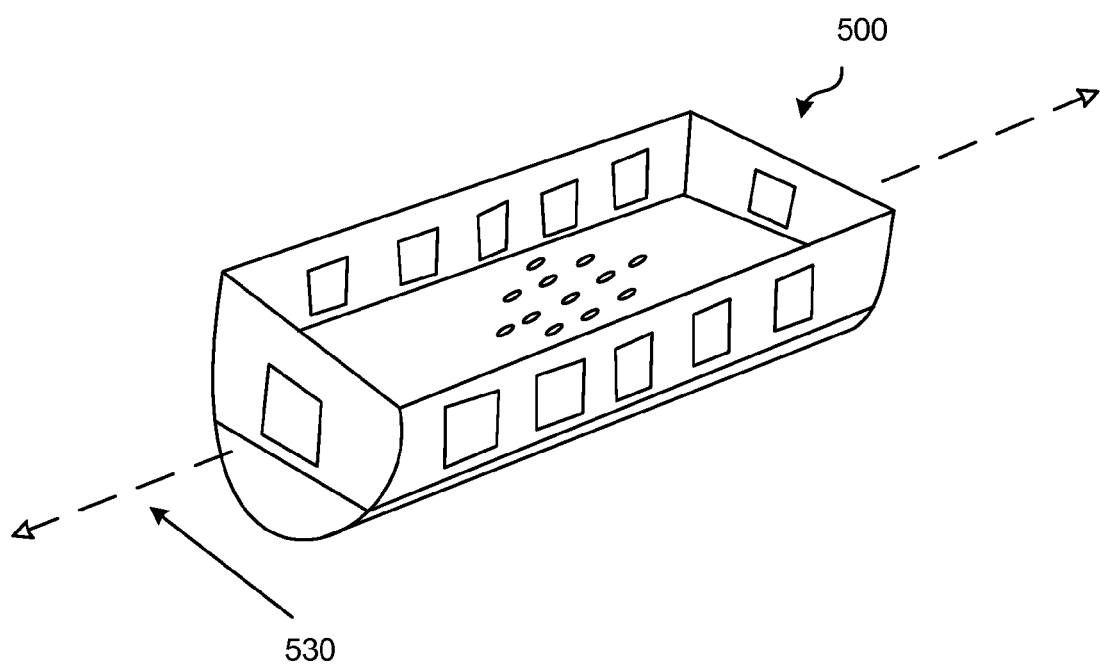
FIG. 14 is a perspective view of a ground contact device according to a sixth embodiment of the presently disclosed subject matter, similar to the fifth embodiment except with one end opening.

Modules 101, 201 and 109, 209 have a generally curved shape. Ground contact device 100, 200 depicted in FIGS. 2 and 3 shows base module 109, 209 having its entire periphery coextensive with the entire periphery of wall module 101, 201 when wall planar member 103, 203 and base planar surface 113, 213 are coupled. Modules 101, 201 and 109, 209 may have any suitable shape or configuration with a rounded portion which can be rolled against a surface—affording a substantially smooth transition between a position where longitudinal axis 123, seen in FIG. 8, is parallel to a weight bearing surface, and a position where longitudinal axis 123 is normal to a weight bearing surface.

Figure 6:
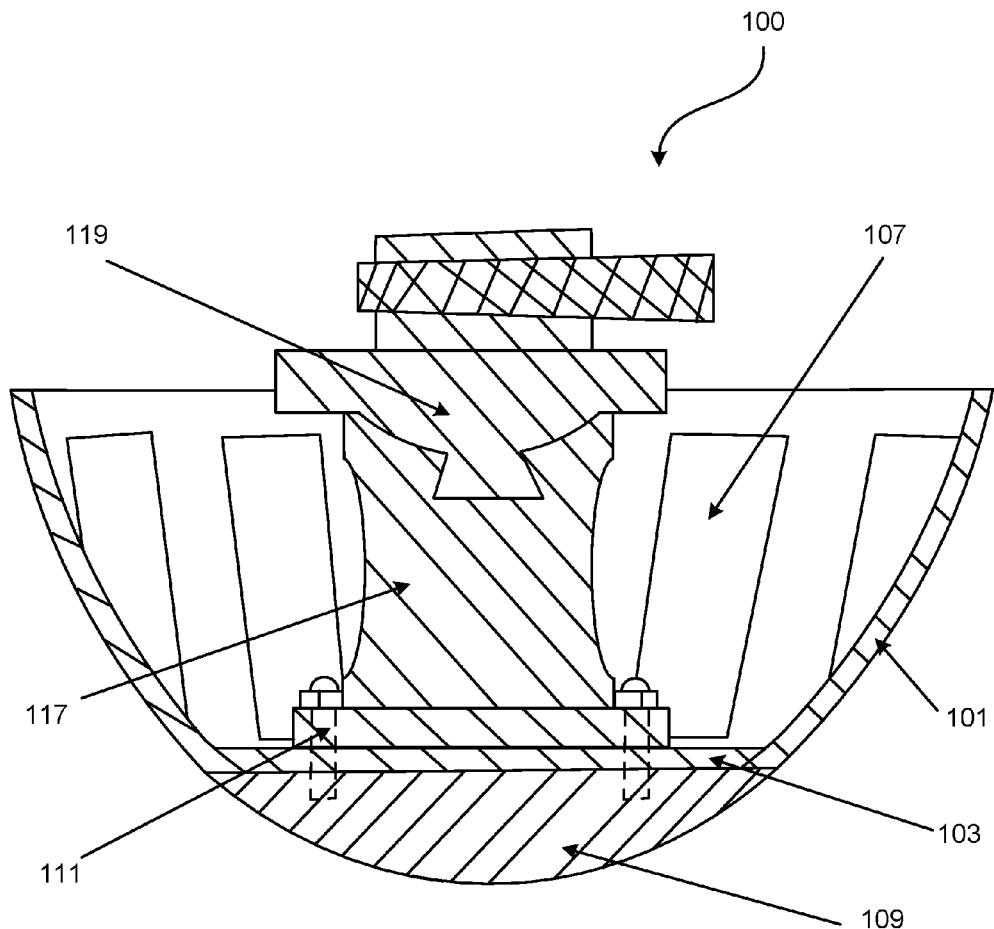
FIG. 6 is a cross sectional view of the ground contact device according to FIG. 1, the ground contact device coupled to a relatively long prosthetic mount.
Figure 7:
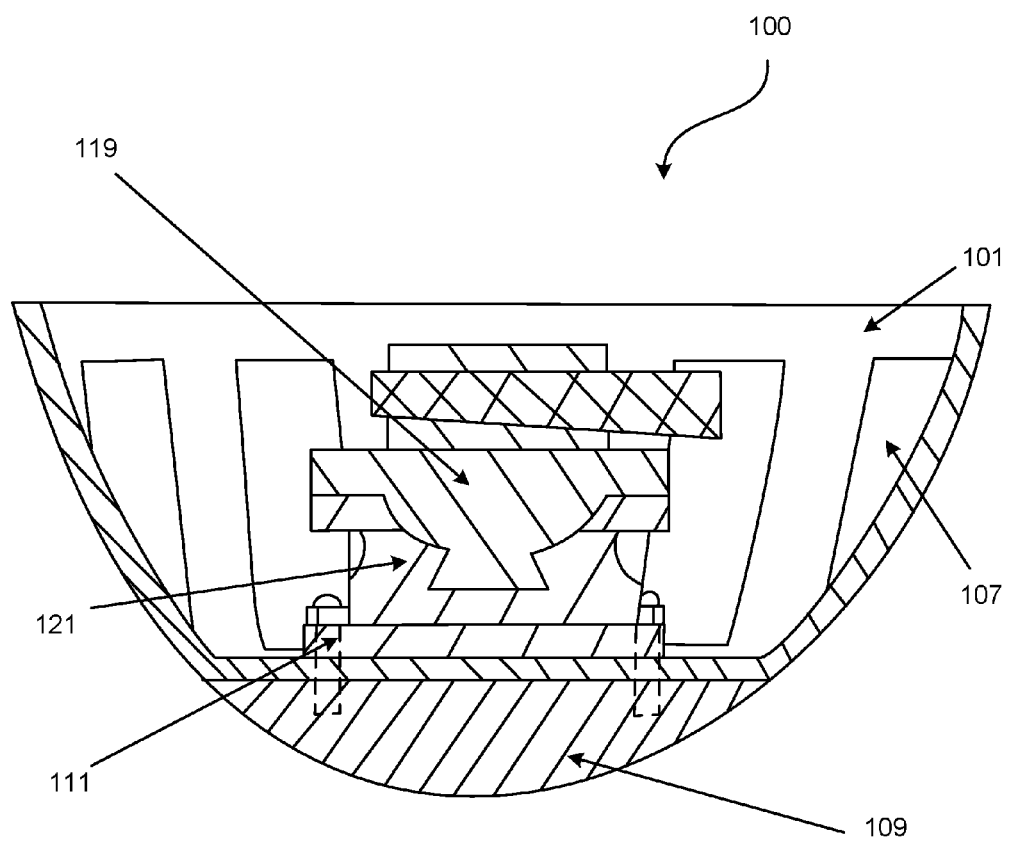
FIG. 7 is a cross sectional view of the ground contact device according to FIG. 1, the ground contact device coupled to a relatively short prosthetic mount.

FIGS. 6 and 7 illustrate the first embodiment with the addition of coupler 111 comprising either prosthetic mount 117 (FIG. 6) or prosthetic mount 121 (FIG. 7). Modules 101 and 109 are shown, in FIG. 6, to comprise coextensive peripheries.

FIG. 6 illustrates ground contact device 100 coupled to coupler 111 including prosthetic mount 117 and prosthetic coupler 119, such as a Ferrier Coupler manufactured by Ferrier Coupler, Inc. Planar member 103 may be of any diameter which provides sufficient area to couple coupler 111 to module 101. Planar member 103 is represented as four-and-one-quarter inches in diameter in FIG. 2. Planar member 103 may be oriented at any angle which allows coupler 111 to couple to planar member 103.

As seen in FIG. 7, ground contact device 100 may be coupled to coupler 111 including prosthetic mounts having varying lengths. Prosthetic mount 117 and prosthetic mount 121 are interchangeable. Prosthetic mount 121 is shorter than prosthetic mount 117, demonstrating that bilateral above-knee amputees and robots with different length limbs may use the ground contact device coupled to different length prosthetic mounts without interfering in the performance of the ground contact device.

Mount holes 105 provide a way to couple prosthetic mount 117 or 121 to planar surface 103 and allow for prosthetic mount 117 or 121 to be adjusted according to the needs of the user. Prosthetic mount 117 or 121 may be coupled to prosthetic coupler 119, which in turn may be coupled to a socket.

Wall module 101 may have a diameter of six-and-one-half inches at its widest point, and base module 109 may have a diameter of four-and-one-quarter inches at its widest point. Base module 109 may be coupled to module wall 101 by any suitable method, including but not limited to, adhesion, bonding, and mechanical fasteners, including but not limited to, screws.

Wall module 101 and base module 109, may also be manufactured as a single component comprising either a single material, or more than one material. In the event that wall module 101 and base module 109 are manufactured as a single module, the single module may be manufactured using additive manufacturing processes, machining, casting, forging, any other suitable method, or a combination of any suitable methods. Wall module 101 and base module 109 may also be manufactured separately using additive manufacturing processes, machining, casting, forging, any other suitable method, or a combination of any suitable methods. Additive manufacturing comprises inputting a template in digital format—which may be produced using computer aided design ("CAD") software—into an additive manufacturing machine, which then interprets the input and deposits layers of material onto a platform to create a three dimensional rendering of the template. Wall module 101, and the single module comprising wall module 101 and base module 109, may be manufactured out of any material having the necessary characteristics to support the weight of a user using the ground contact device, including but not limited to, titanium, steel, aluminum, aluminum alloy, iron, carbon fiber, and durable polymer materials. Base module 109 may be manufactured out of any material having suitable structural integrity such as, but not limited to, foam, closed pore polyurethane, titanium, steel, aluminum, aluminum alloy, iron, carbon fiber, and durable polymer materials.

Figure 4:
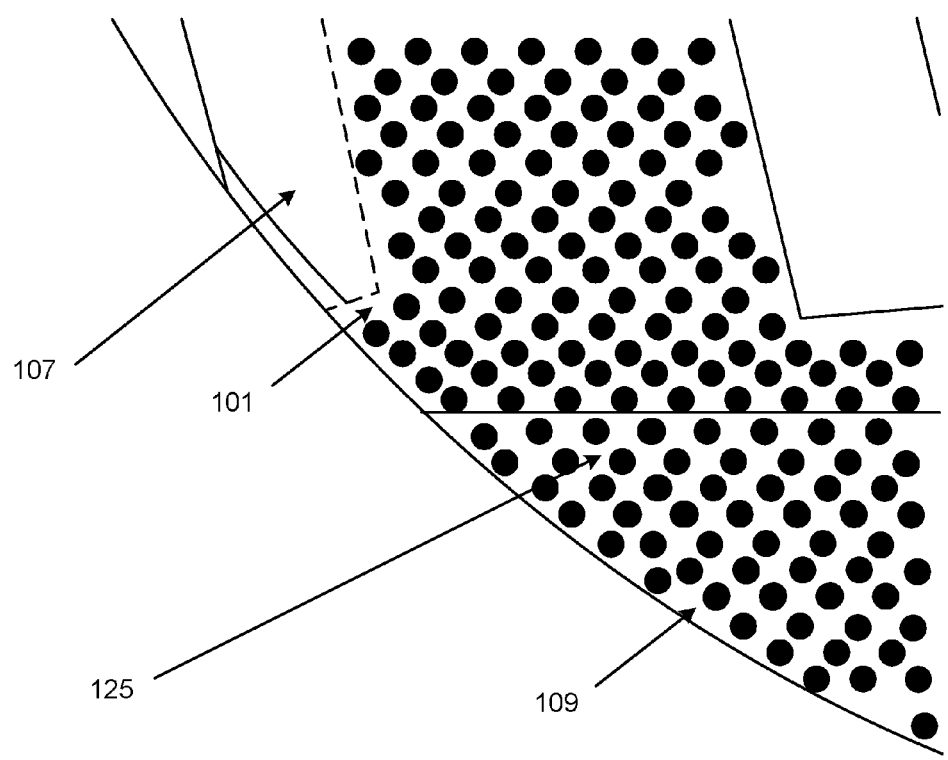
FIG. 4 is an enlarged view of the encircled area designated 4 in FIG. 3, showing an alternative roughened surface of the ground contact device.

FIG. 4 is an enlarged view of wall module 101 and base module 109, but having a roughened layer, or outer surface, 125. Roughened layer 125 may be created by methods including but not limited to manipulating the material of pre-manufactured modules 101 and 109, removing material from modules 101 and 109 to create depressions, affecting the cast used to manufacture modules 101 and 109 to create depressions or projections, or by applying additional material to modules 101 and 109. Polymers, such as those used in pickup truck beds, may be applied to modules 101 and 109 to create the roughened layer. The roughened layer may also comprise a layer of tacky material that may be smooth or have depressions and/or projections which may be comprised of material including but not limited to smooth closed pore polyurethane.

Figure 18:
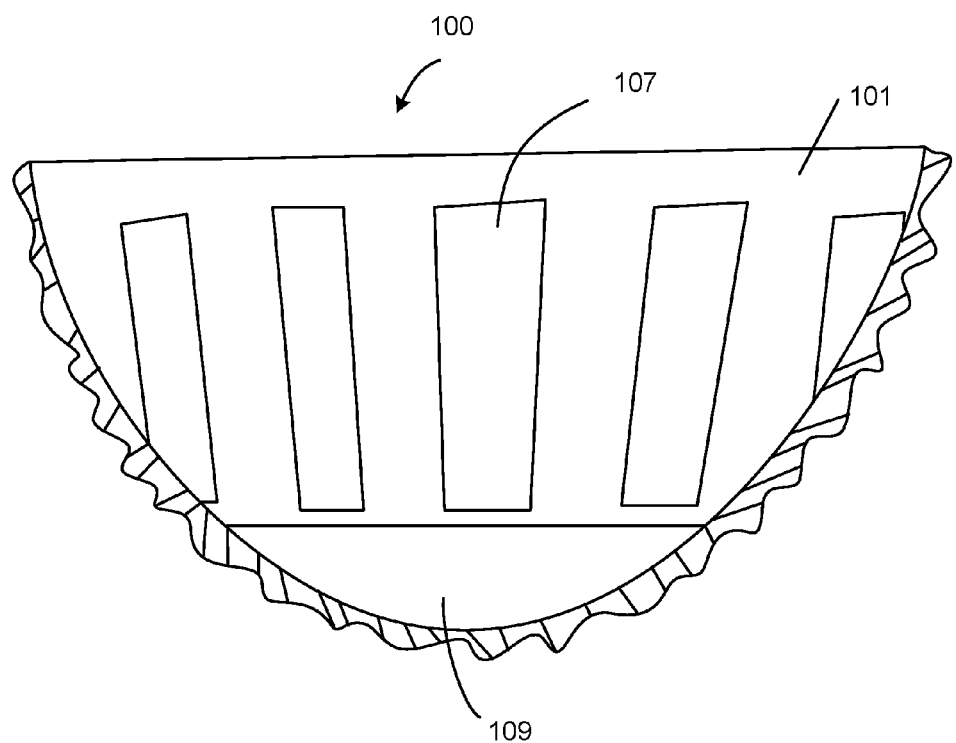
FIG. 18 is a cut away view of a ground contact device according to the first embodiment of the presently disclosed subject matter with an alternative surface treatment.

FIG. 18 is a cut away view of a ground contact device 100 except that outer surfaces of wall module 101 and base module 109 are wavy or have bumps or nipples. Wall module 101 and base module 109 need not have the same pattern of waves, bumps or nipples. Of course, either wall module 101 or base module 109 can have waves, bumps or nipples. Openings 107 are also depicted in FIG. 18.

Figure 5:
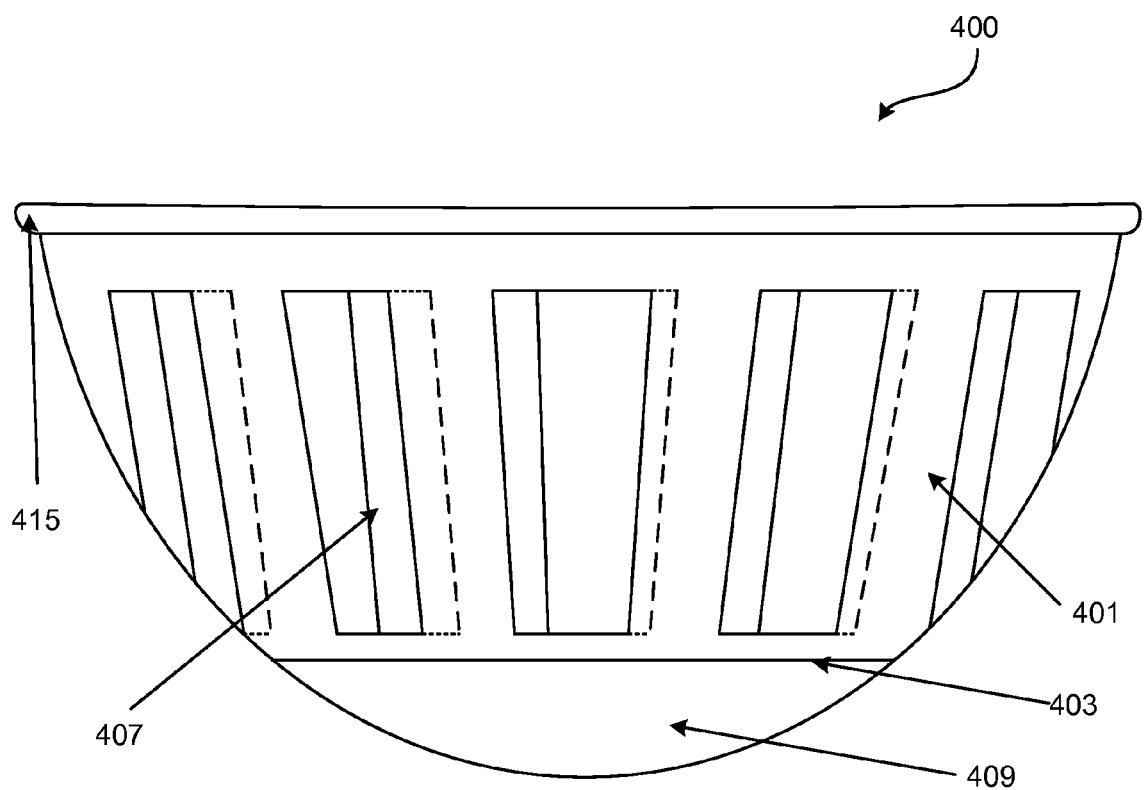
FIG. 5 is a side elevational view of a ground contact device according to a third embodiment of the presently disclosed subject matter.

FIG. 5 depicts ground contact device 400, similar to ground contact device 100, having flange 415. Flange 415 is shown as a contiguous extension of wall module 401, and may be manufactured as a single component with wall module 401. Flange 415 may also be a component manufactured separate from wall module 401, and then later coupled to wall module 401 through suitable methods such as, but not limited to, welding. Flange 415 may be manufactured out of materials including but not limited to foam, closed pore polyurethane, titanium, steel, aluminum, aluminum alloy, iron, carbon fiber, and durable polymer materials.

Figure 19:
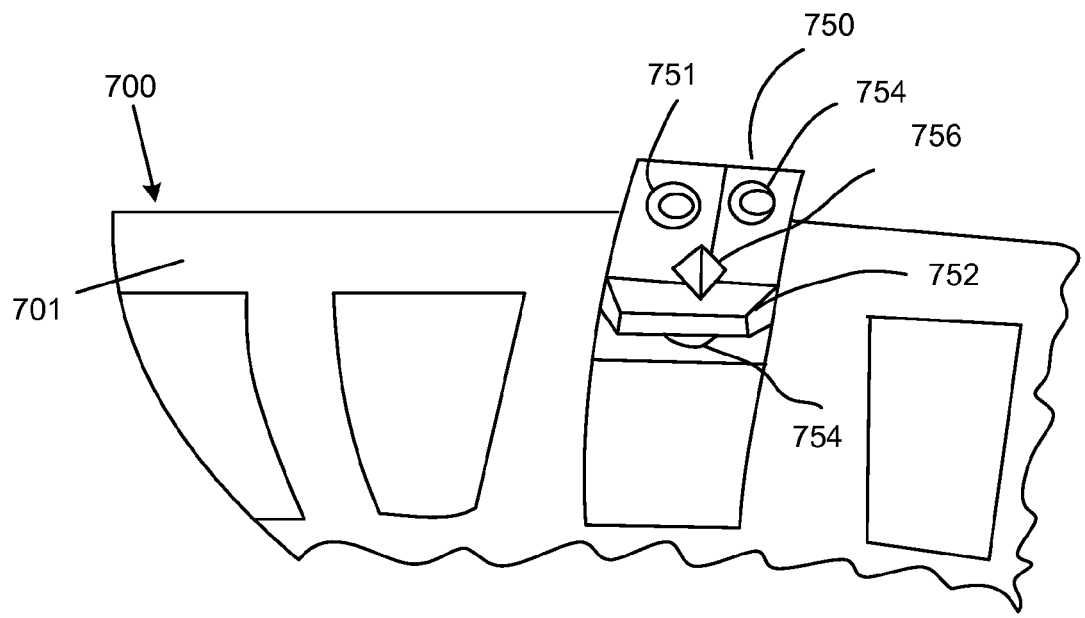
FIG. 19 is a front elevational view of a ground contact device according to an eighth embodiment of the presently disclosed subject matter.
Figure 20:
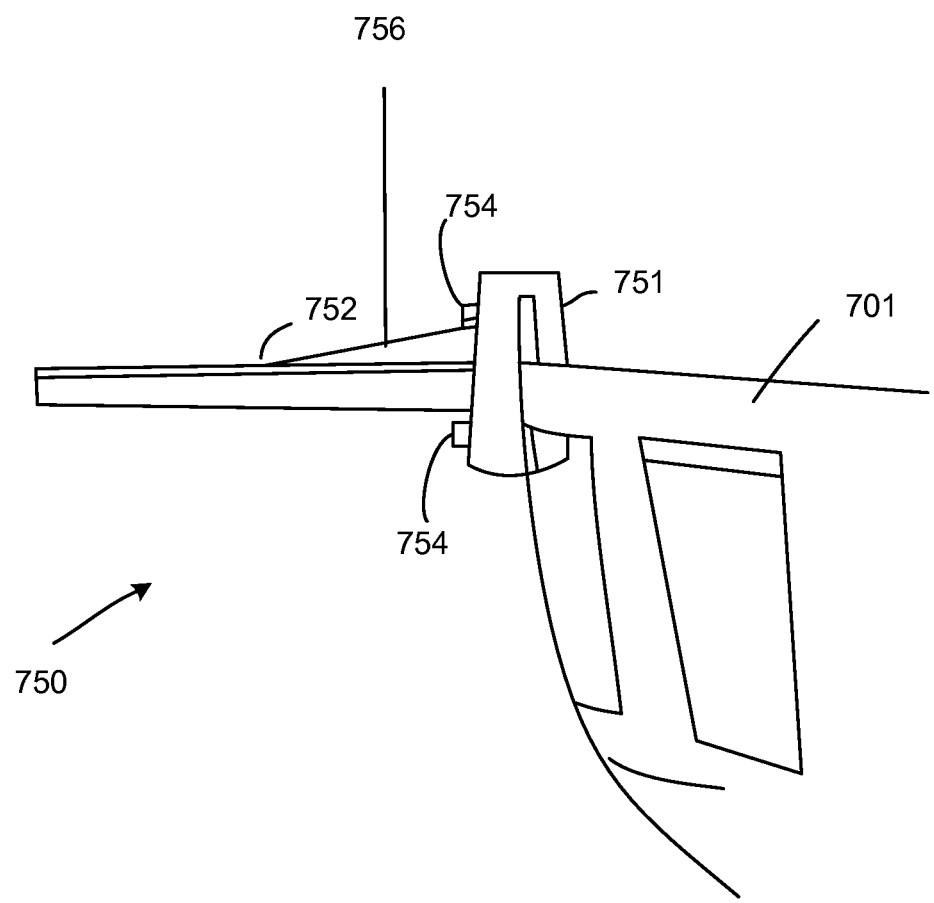
FIG. 20 is a side elevational view of the ground contact device according to FIG. 19.
Figure 21:
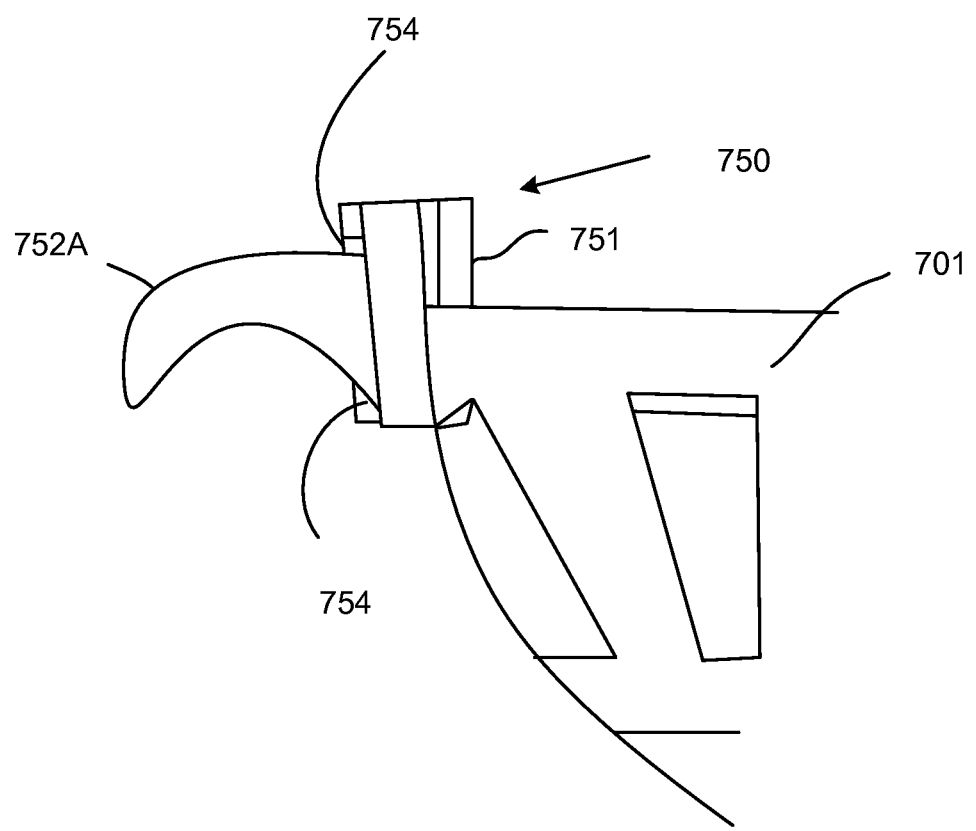
FIG. 21 is a front elevational view of a ground contact device according to the eighth embodiment of the presently disclosed subject matter with an alternative hook.

FIGS. 19-21 show ground contact device 700 with attachment 750. Attachment 750 includes clamp 751 that attaches to wall module 701 by bolts 754. Extending outwardly from clamp 751 and wall module 701 is a protrusion, such as spike 752. In FIG. 21, the protrusion is illustrated in the form of hook 752A. Of course, the protrusion can take any shape. Attachment 750 may be employed to assist the wearer of ground contact device 700 to traverse terrain otherwise difficult or impossible with ground contact device 700. Examples might include mountain climbing or ice traversing/climbing.

Ground contact device 500 in FIGS. 10-14 comprises wall module 501 which is analogous to wall module 101 of ground contact device 100. Wall module 501 has a shape that is partially cylindrical, with the longitudinal axis 530 (FIG. 14) of the module parallel to a weight bearing surface.

Figure 15:
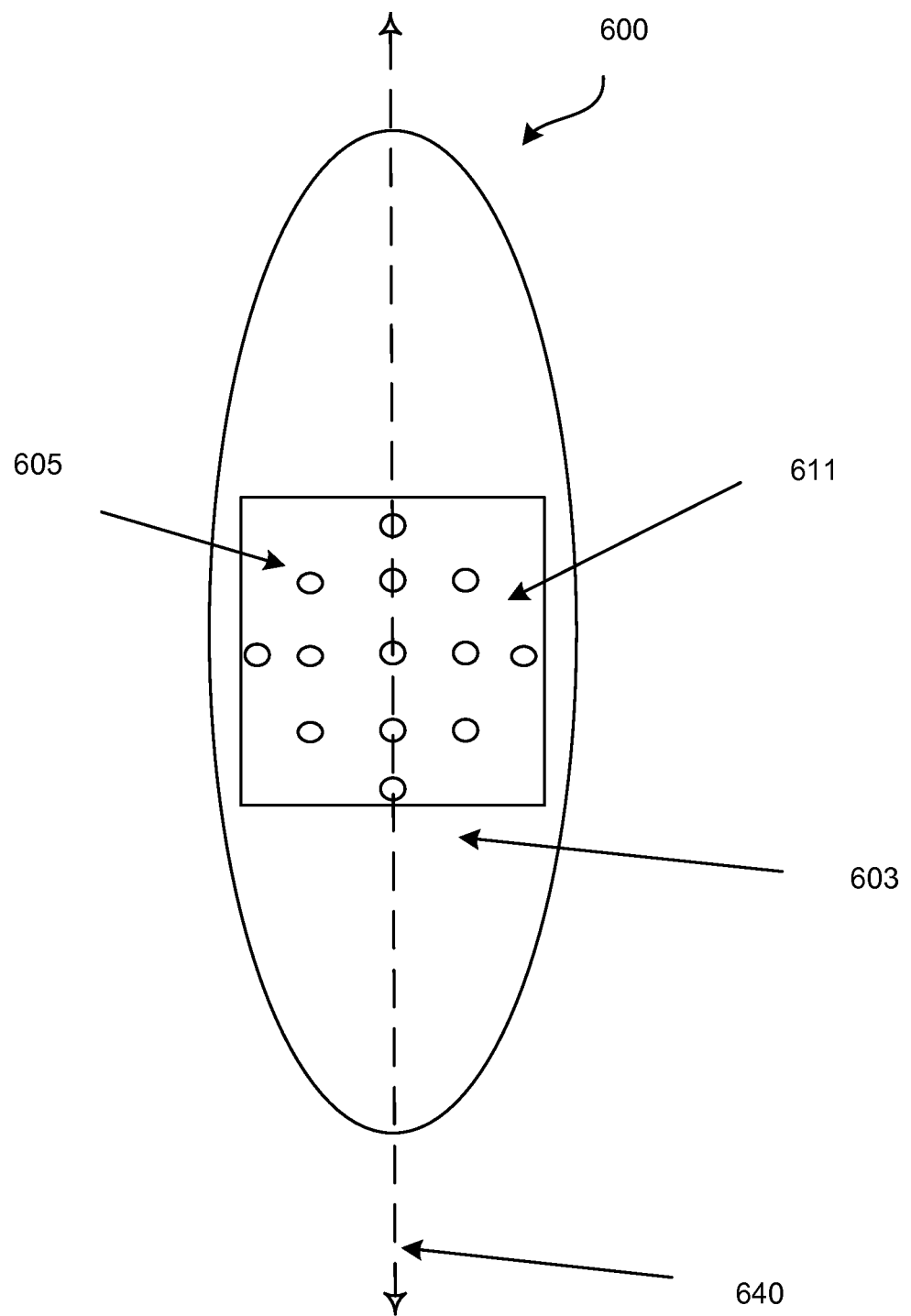
FIG. 15 is a top plan view of a ground contact device according to a seventh embodiment of the presently disclosed subject matter.
Figure 16:
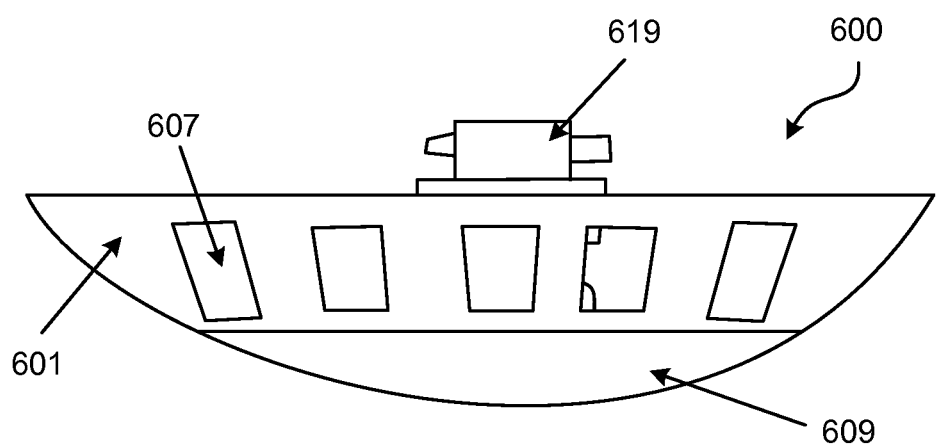
FIG. 16 is a side elevational view of a ground contact device according to the seventh embodiment of the presently disclosed subject matter with a prosthetic mount.
Figure 17:
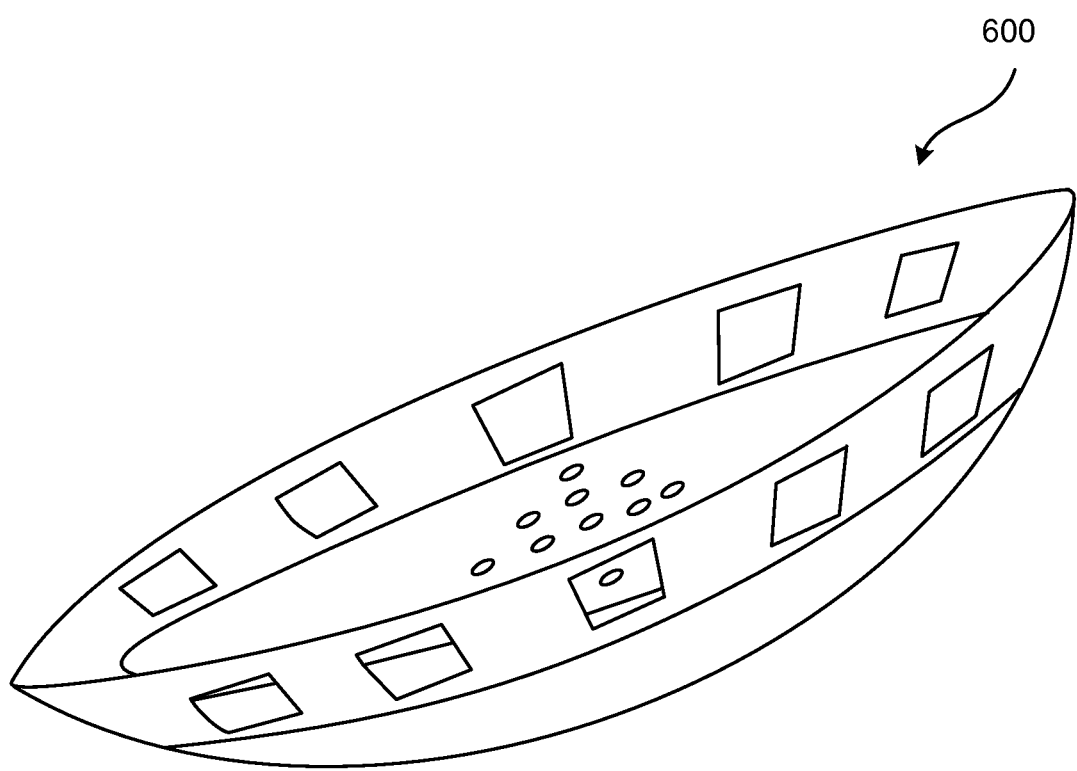
FIG. 17 is a perspective view of a ground contact device according to the seventh embodiment of the presently disclosed subject matter.

Ground contact device 600, in FIGS. 15-17, comprises wall module 601 which is analogous to wall module 101 of ground contact device 100. Wall module 601 is partially rounded and elongated along longitudinal axis 640 (FIG. 15). An elongated ground contact device, such as embodiment 600, may aid a user in transitioning from a prone position to a standing position. The mount holes 605 may be placed anywhere along the longitudinal axis 640 such that the coupler 611 may be coupled to module 601.

Wall modules 101, 201, 401, 501 and 601 may consist of a number of independent members having partially curved surfaces which are connected by, and to, planar surfaces 103, 203, 403, 503 and 603, respectively. Wall modules 501 and 601 may be manufactured out of any material having the necessary characteristics to support the weight of a user using the ground contact device, including but not limited to, titanium, steel, aluminum, aluminum alloy, iron, carbon fiber, and durable polymer materials. Wall modules 501 and 601 may be manufactured using additive manufacturing processes, machining, casting, forging, any other suitable method, or a combination of any suitable methods.

The ground contact device may be used to transition the user from a prone or seated position to a standing position. The user may transition from a seated or prone position by leveraging his/her torso, or body of a machine in the case of robotic applications, over the ground contact device. This may be done by using an arm to push the user, or machine, over the ground contact device, while rolling, for example, base module 109 and wall module 101 (or the singular module) against the ground, creating friction which holds the ground contact device in place and allows the user to position their center of gravity over the ground contact device.

In this specification, "a" and "an" and similar phrases are to be interpreted as "at least one" and "one or more." References to "an" embodiment in this disclosure are not necessarily to the same embodiment. In this specification, "user" and similar phrases are to be interpreted as any "animal," "person," "machine," or "robot" coupled to the ground contact device.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element) or a combination thereof, all of which are behaviorally equivalent.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that the disclosed subject matter may be embodied in other specific forms without departing from the spirit or essential characteristics thereof. The embodiments described above are therefore to be considered in all respects as illustrative—not restrictive. The scope of the disclosed subject matter is indicated by the appended claims rather than by the foregoing description, and all changes which come within the meaning and range of equivalency of the claims are therefore intended to be embraced therein. In fact, after reading the above description, it will be apparent to one skilled in the relevant art(s) how to implement alternative embodiments. Thus, the present embodiments should not be limited by any of the above described exemplary embodiments. However, one skilled in the art will recognize that embodiments of the invention could comprise flange 415 having a square or triangular shape.

In addition, it should be understood that any figures that highlight any functionality and/or advantages, are presented for example purposes only. The disclosed architecture is sufficiently flexible and configurable, such that it may be utilized in ways other than that shown. For example, the presently disclosed subject matter may be used in conjunction with a machine or robot.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A prosthetic ground contact device, comprising:
    a base module comprising:
        a planar surface, and
        a convex rounded ground engaging surface;
    a wall module comprising:
        a planar member having an entire periphery coextensive with an entire periphery of the planar surface, and
        an outer wall surrounding the planar member and extending from the planar member away from the base member, at least a portion of the outer wall being curved so as to continue the convex curvature of the rounded ground engaging surface; and
    a prosthetic mount coupled to the planar member.

2. The ground contact device according to claim 1, wherein the wall module defines:
    a plurality of openings through the outer wall.

3. The ground contact device according to claim 1, wherein the planar member includes a plurality of threaded holes by which the prosthetic mount is coupled to the planar member.

4. The ground contact device according to claim 1, wherein at least a portion of an outer layer of the outer wall of the wall module and the base module is roughened.

5. The ground contact device according to claim 1, wherein at least a portion of an outer layer of the outer wall of the wall module is roughened.

6. The ground contact device according to claim 1, wherein at least a portion of an outer layer of the base module is roughened.

7. The ground contact device according to claim 1, wherein the wall module comprises:
    a flange extending beyond a rim of the outer wall of the wall module.

8. The ground contact device according to claim 1, wherein the outer wall of the wall module is at least partially cylindrical.

9. The ground contact device according to claim 1, wherein the outer wall of the wall module is at least partially elliptical in shape.

10. The ground contact device according to claim 8, further comprising;
    prosthetic coupler coupled to the prosthetic mount.

11. The ground contact device according to claim 1, wherein an outer surface of the wall module and/or the base module includes waves, bumps or nipples.

12. The ground contact device according to claim 1, further comprising an attachment coupled to the wall module, the attachment including a protrusion extending outwardly from the wall module.

\* \* \* \* \*